United States Patent [19]
Nathanson et al.

[11] Patent Number: 6,074,343
[45] Date of Patent: Jun. 13, 2000

[54] SURGICAL TISSUE RETRACTOR

[76] Inventors: Michael Nathanson, 5315 Silver Point Way, San Jose, Calif. 95138; Tibor B. Koros; Gabriel J. Koros, both of 610 Flinn Ave., Moorpark, Calif. 93021

[21] Appl. No.: 09/294,998

[22] Filed: Apr. 16, 1999

[51] Int. Cl.[7] .................................................. A61B 17/02
[52] U.S. Cl. .......................................... 600/214; 600/224
[58] Field of Search .................................. 600/214, 224, 600/225, 219, 228, 229, 210, 184

[56] References Cited

U.S. PATENT DOCUMENTS

| | | | |
|---|---|---|---|
| 351,548 | 10/1886 | Watson | 600/224 |
| 817,973 | 4/1906 | Hausmann | 600/224 |
| 2,374,863 | 5/1945 | Guttmann | 600/224 |
| 2,608,192 | 8/1952 | Heitmeyer et al. | 600/229 |
| 3,680,546 | 8/1972 | Asrican | 600/219 |
| 3,810,462 | 5/1974 | Szpur | 600/228 |
| 4,380,999 | 4/1983 | Healy | 600/228 |
| 4,991,566 | 2/1991 | Shulman et al. | 600/224 |
| 5,307,805 | 5/1994 | Byrne | 600/214 |
| 5,339,801 | 8/1994 | Poloyko et al. | 600/214 |
| 5,776,054 | 7/1998 | Bolora | 600/219 |

*Primary Examiner*—Paul J. Hirsch
*Attorney, Agent, or Firm*—David O'Reilly

[57] ABSTRACT

A surgical tissue retractor for use in small tissue incisions such as heart valve surgery. The retractor is comprised of a plurality of retractor blades that can be operated simultaneously or at least one or more blades can be operated independently. Right and left retractor blades are mounted on an actuator mechanism that spreads or expands the blades as a rotatable primary actuator knob is rotated. A third retractable arm is mounted for simultaneous operation with the right and left retractor blade or independent operation through a secondary rotatable actuator knob that extends or retracts a threaded shaft attached to the center retractor blade. The retractor includes a housing having a hangar for use of the retractor in conjunction with a larger retractor such as a sternum spreader or rib spreader retractor.

15 Claims, 6 Drawing Sheets

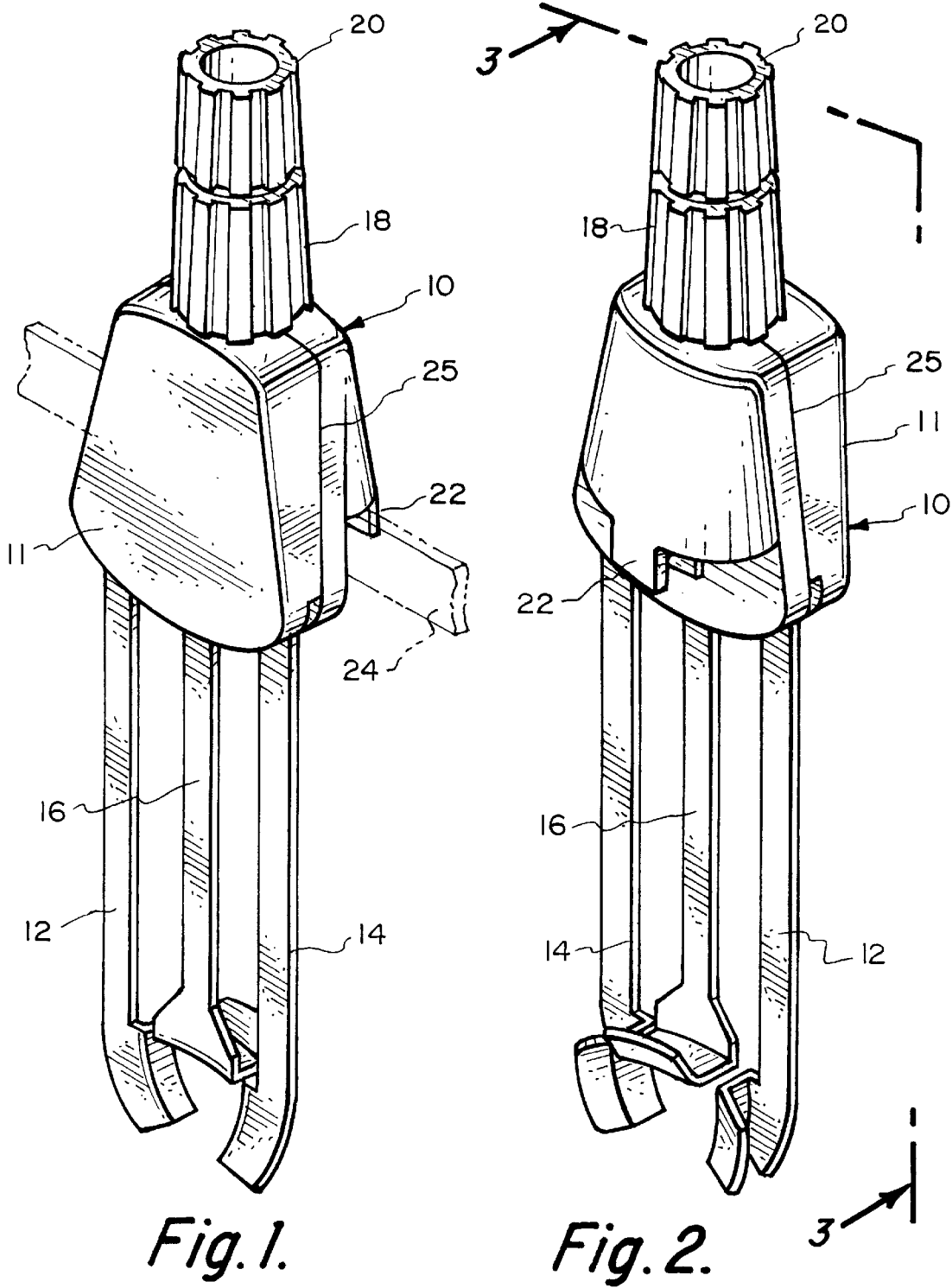

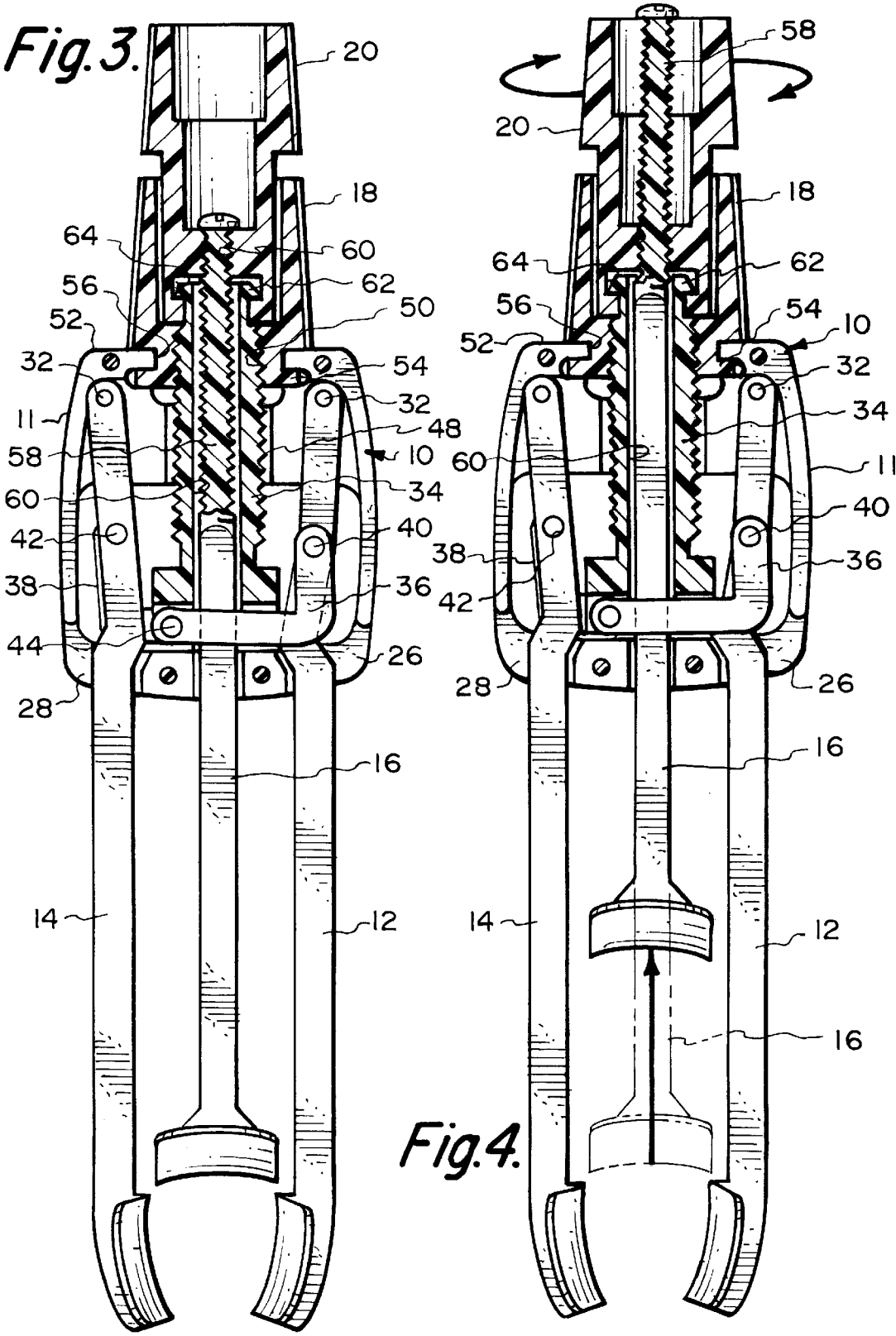

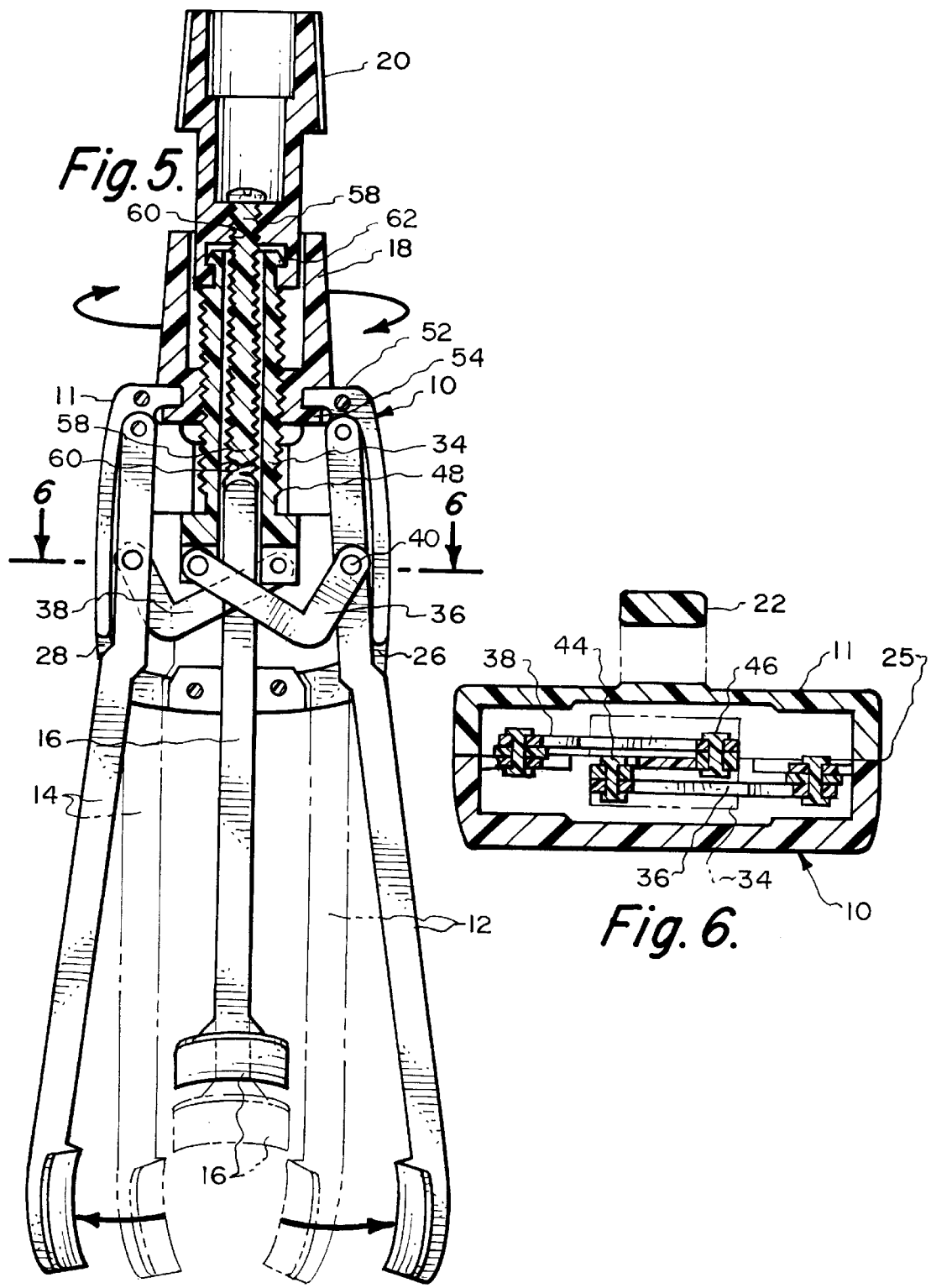

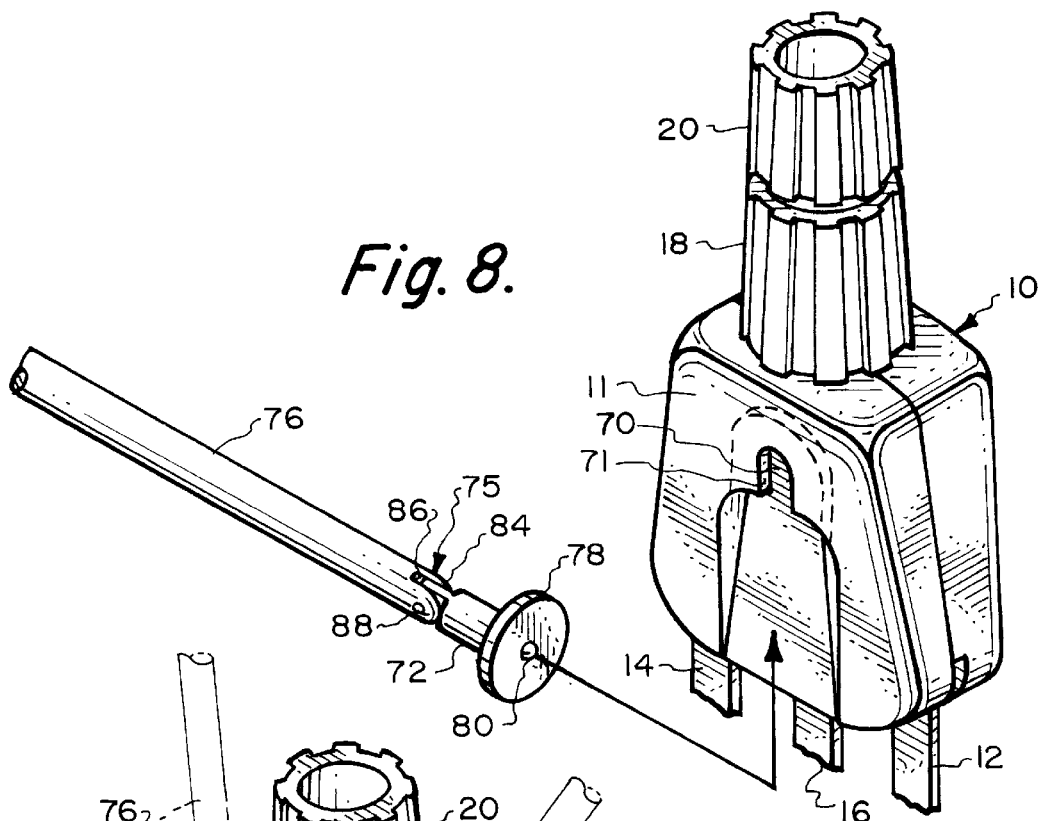
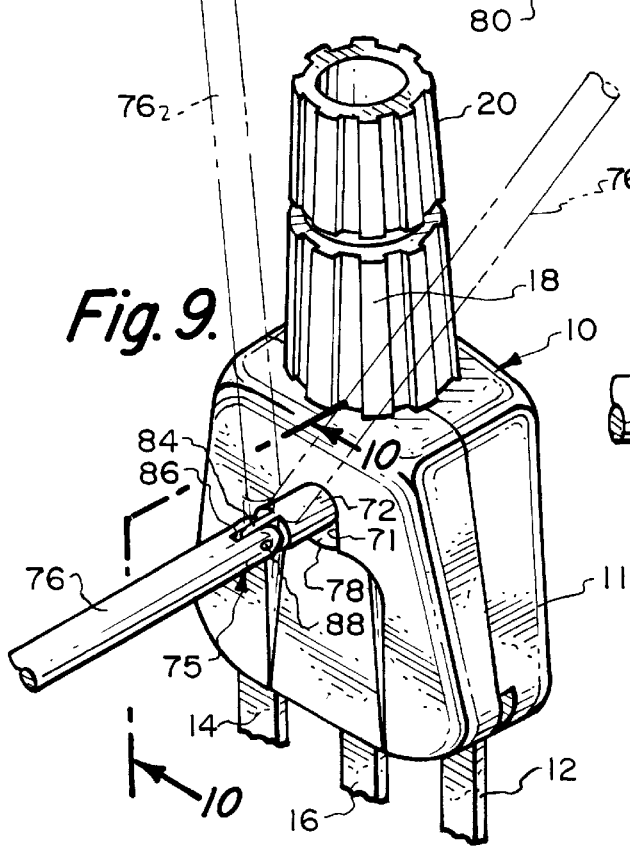
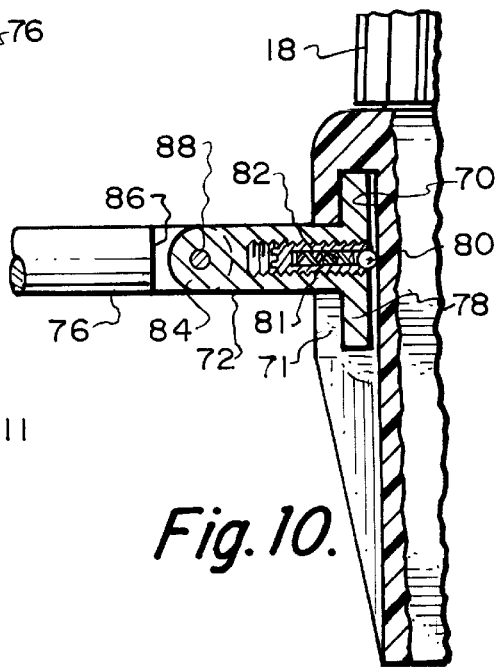
Fig. 8.
Fig. 9.
Fig. 10.

SURGICAL TISSUE RETRACTOR

BACKGROUND OF THE INVENTION

1. Field of the Invention

This invention relates to surgical tissue retractors and more particular relates to a small easily manipulated retractor having expandable blades that are for tissue retraction in small incisions such as heart valve surgery.

2. Background Information

There are a number of types of small retractors available for a variety of surgery. For example, there are eye speculum retractors such as the Maumenee-Park eye specular comprised of a pair of parallel blades that expand away from each other and a center blade that can be retracted upward. There are also special retractors that work on the same principle as a compass with a screw member expanding a pair of blades away from each other. For example, a Perkins retractor has a pair of curved arms attached to a scissors-like arrangement that can be locked after opening by operation of the handle.

Another type of small retractor is called a Dingman mouth gag such as that shown and described in U.S. Pat. No. 4,024,859. This device has traversed bar with a centrally mounted tongue retractor and clamp means at opposite ends for adjustably supporting alveolar retractors. There are also mechanically expandable retractors for use in arthroscopic surgery that can be passed through a trocar. The retractor is formed in a long thin tube having a plurality of fingers at the end that can be opened and closed by operation of a trigger-like arrangement at the outer end. The small trigger expandable retractors are generally used for arthroscopic surgery for passing through a puncture. One such device is shown and described in U.S. Pat. No. 5,195,506. While these devices are effective for the specific purpose intended, none of these are entirely suitable for use in small incisions such as those that occur during heart valve surgery.

It is therefore one object of the present invention to provide an improved surgical tissue retractor for use in small incisions in tissue.

Still anther object of the present invention is to provide a surgical tissue retractor having a plurality of expandable blades that may be used in conjunction with a larger retractor.

Still another object of the present invention is to provide a surgical tissue retractor having a plurality of expandable blades that is particularly suited for use in heart valve surgery.

Still another object of the present invention is to provide a surgical tissue retractor having a plurality of expandable blades with the blades being manipulated simultaneously or at least one blade being manipulated independently.

Still another object of the present invention is to provide a surgical tissue retractor having a pair of adjacent blades that expand outwardly and a center blade that can be manipulated independently to retract an incision for desired exposure.

Yet another object of the present invention is to provide a surgical tissue retractor having a plurality of expandable blades with a hanger for securing the tissue retractor to an arm of a larger retractor.

BRIEF DESCRIPTION OF THE INVENTION

The purpose of the present invention is to provide a surgical tissue retractor having a plurality of expandable blades with a mechanism for simultaneously spreading the plurality of blades or independently operating at least one of the blades.

The surgical tissue retractor of the present invention is comprised of a housing having a threaded hollow actuator shaft attached by articulating links or braces to a pair of solid expandable blades. A third blade secured at an end to a threaded shaft passing through the hollow threaded actuator tube. A primary rotable knob seated at an upper end of the housing is threaded on the threaded hollow actuator tube for raising and lowering the tube.

Rotation of the primary rotable knob raises and lowers the threaded tube which simultaneously expands or spreads the retractor blades. The first pair of retractor blades are expanded by manipulation of links or braces that are pivotally attached to one end of the threaded hollow tube and at the other end to the retractor blade. The links are formed at right angles to provide a scissors-like action to actuate or spread the first pair of retractor blades.

A third blade is attached to a threaded shaft inside the threaded hollow tube and connected to a second rotatable actuator knob mounted on top of and concentric with the first rotatable knob. This arrangement allows the third retractor blade to be separately manipulated by the rotation of the second rotatable actuator knob. Rotation of the second rotatable knob causes the threaded shaft to be retracted into the bore of the hollow tube actuating and spreading the third retractor blade. Thus, the plurality of blades can be operated simultaneously or the center blade can be operated independently to retract an incision. An important feature of the invention is the blades are constructed and arranged to provide a clear view of a surgical site when the retractor is positioned in an incision and the blades are expanded or spread.

The surgical tissue retractor is particularly suited for retracting tissue in small incisions such as heart valve operations. The retractor includes a hanger on the housing for mounting the retractor on a larger retractor such as a sternum or rib spreader used during heart valve surgical procedures. One such retractor for use in heart valve surgery is shown and disclosed in U.S. Pat. No. 5,167,223 issued Dec. 1, 1992 to the same inventors as those listed herein.

In an optional but preferred embodiment of the invention the hangar is replaced with a socket on the rear of the retractor housing for receiving a post having a base plate that seats in the socket. A retractor rod is connected to the post by a hinge. The rod includes a clamp for mounting the retractor on an arm of a larger retractor. This arrangement allows the surgical tissue retractor to be pivoted and swiveled on the connection to properly position it in an incision.

In use, the retractor is very effective in providing optimal access to a surgical site in small incisions such as those of performing heart valve surgery. The retractor is placed in incision and can be manipulated to expand the blades with the center blade being separately manipulated, if desired. The blades are expanded by rotation of the primary rotable actuating knob which retracts the threaded actuator tube to expand right and left side arms through actuator braces or links that are pivotally attached by pins. The center blade can then the separately manipulated by a secondary center rotable actuator knob to expand the incision further.

Another optional but preferred embodiment includes the attachment of auxiliary blades secured to the side blades that can be manually adjusted. The blades are attached by means of a series of detents in the side blades for repositioning the auxiliary blades in an incision.

The above and other novel features of the invention will be more fully understood from the following detailed description and the accompanying drawings, in which:

BRIEF DESCRIPTION OF THE DRAWINGS

FIG. 1 is a front, isometric view of a surgical tissue retractor according to the invention.

FIG. 2 is a rear isometric view of the surgical tissue retractor according to the invention.

FIG. 3 is a sectional view taken at 3—3 of FIG. 2.

FIG. 4 is a sectional view similar to FIG. 3 illustrating independent operation of the center blade of the surgical tissue retractor.

FIG. 5 is another sectional view similar to FIG. 3 illustrating simultaneously operation of all blades of the surgical tissue retractor.

FIG. 6 is a sectional view taken at 6—6 of FIG. 5.

FIG. 8 is a partially exploded view illustrating an optional embodiment of surgical tissue retractor according to the invention.

FIG. 9 is a rear view of the surgical tissue retractor illustrating operation of the optional embodiment.

FIG. 10 is a sectional view taken at 10—10 of FIG. 9.

DETAILED DESCRIPTION OF THE INVENTION

Figure 7:
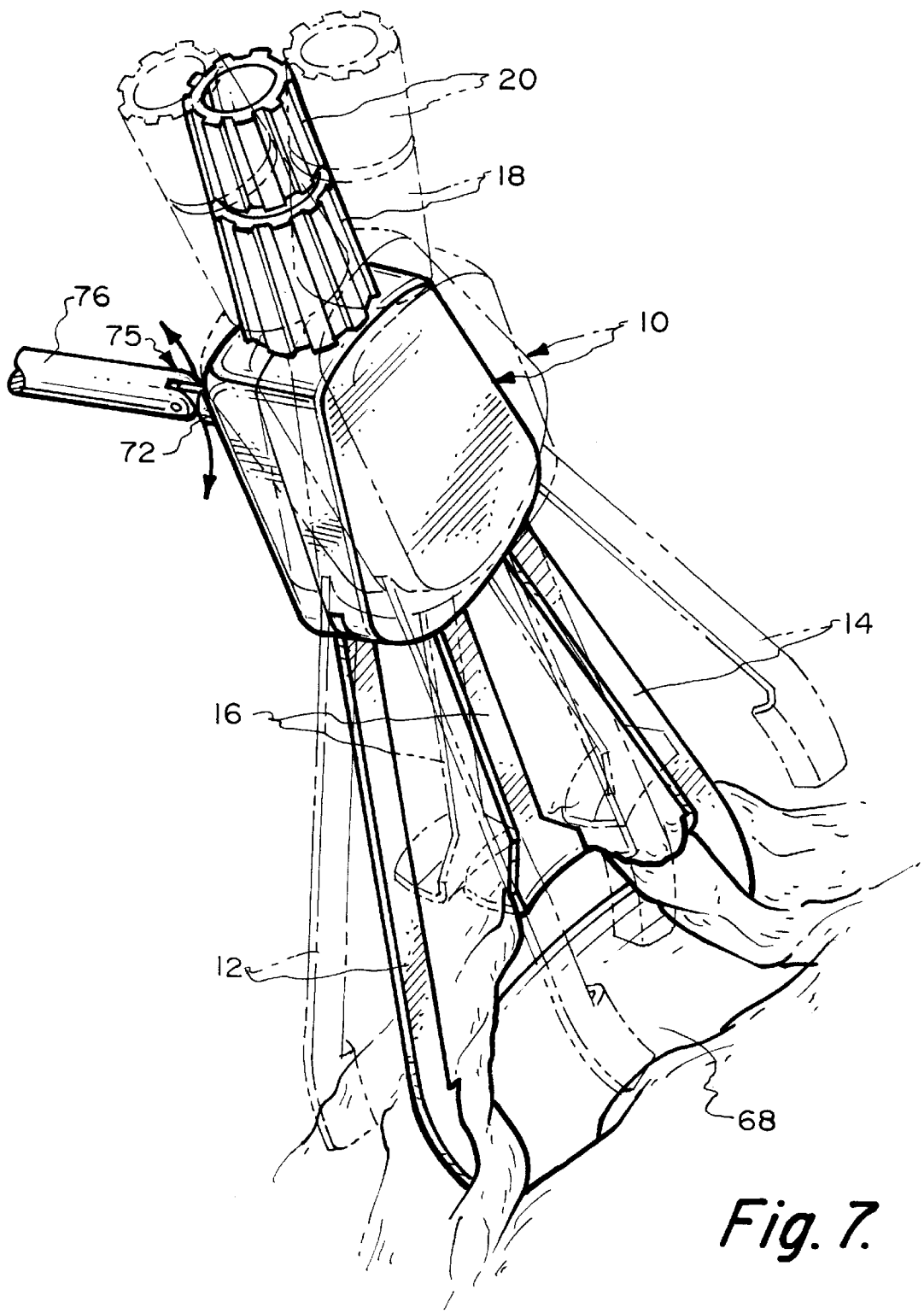
FIG. 7 is an isometric view of an optional embodiment illustrating placement and operation of the surgical tissue retractor.

A surgical tissue retractor according to the invention is illustrated in isometric views of FIGS. 1 and 2. Surgical tissue retractor 10 is comprised of a housing 11 having right and left side arms or blades 12 and 14 and center blade 16. Center blade 16 may be manipulated or retracted independent of right and left sides retractor blades 12 and 14 as will be described in greater detail hereinafter. Surgical tissue retractor 10 is constructed for use with larger retractors such as sternum or rib spreaders and includes a hanger 22 for mounting tissue surgical retractor 10 on an arm or bar 24 of a sternum or rib spreader retractor.

Retractor blades 12, 14, and 16 may be simultaneously retracted or spread by operation of primary rotable actuator knob 18 while center blade 16 may be independently retracted by secondary rotable knob 20. Blades 12, 14, and 16 can have blade ends or flanges constructed to be solid, fenestrated, or any configuration desired. Additionally, blades 12, 14, and 16 could be segmented blades providing a multi-blade construction that expands much in the manner that the petals of a flower open. As primary rotatable actuator knob 18 is operated, blades 12, 14, and 16 constructed in segmented sections will be simultaneously spread to retract an incision.

The construction of surgical tissue retractor 10 is illustrated in the sectional view of FIG. 3. Surgical retractor 10 is formed of a two-piece housing 11 constructed of metal, plastic, or any other suitable material joined together at a junction 25 by any suitable means. Right and left retractor blades 12 and 14 extend through openings or slots 26 and 28 through the bottom of housing 11 and are secured by pivot pins 32 that allow right and left retractor blades 12 and 14 to spread or expand.

Right and left side retractor blades 12 and 14 are connected to a threaded tubular actuator 34 attached to the blade by actuator links or braces 36 and 38. Actuator links 36 and 38 are connected to right and left retractor blades 12 and 14 by pivot pins 40 and 42 and to actuator tube 34 by pivot pins 44 and 46 (FIG. 6). Threads 48 on actuator tube 34 engage threads 50 inside primary rotary knob 18. Primary rotary knob 18 is mounted in upper end 52 of housing 11 by collar 54 seated in aperture 56 in upper end 52 of housing 11. This allows primary rotary knob 18 to freely rotate in housing 11. Rotation of primary rotary actuator knob 18 retracts or withdraws actuator tube 34 upwardly which activates actuator links 36 to spread right and left retractor blades 12 and 14 as will be described in greater detail hereinafter.

Center surgical tissue retractor blade 16 is attached to threaded shaft 58 passing through bore 60 of hollow actuator tube 34. Threaded shaft 58 engages threads 60 in secondary blade actuating knob 20. Rotation of secondary blade actuating knob 20 retracts or withdraws threaded shaft 58 through thread 60 to separately manipulate center retractor blade 16, if desired. Secondary actuator knob 20 is secured to flange 62 on the upper end of actuator tube 34 engaging socket 64 in secondary knob 20. Thus rotation of primary knob 18 retracts simultaneously both right and left side retractor blades 12 and 14 but also center retractor blade 16.

The independent operation of retractor blade 16 is illustrated in FIG. 4. Center retractor blade 16 can be separately manipulated or retracted by rotation of secondary actuator knob 20 which withdraws or retracts center blade threaded shaft 58 into knob 20 as shown in phantom. Rotation of secondary actuator knob 20 extends or retracts center blade 16 independently of right and left surgical tissue retractor blades 12 and 14.

The simultaneous operation of all retractor blades is illustrated in FIG. 5. Rotation of primary actuator knob 18 withdraws actuator tube 34 to operate actuator links 36 and 38 which spreads right and left actuator arms 12 and 14 as illustrated in phantom. Simultaneously secondary actuator knob 20 with threaded shaft 58 are withdrawn with actuator tube 34 also as illustrated in phantom.

The placement of the retractor in tissue such as heart tissue for heart valve surgery is illustrated in FIG. 7. An incision 68 is made in tissue, such as heart tissue adjacent to a heart valve, and blades 12, 14, and 16 placed in incision with the retractor closed as illustrated in FIGS. 1 or 2. The surgeon then has the option of operating primary actuator knob 18 or secondary actuator knob 20 first as desired. If primary actuator knob 18 is rotated first, all three retractor blades 12, 14, and 16 will be retracted or spread with the ends engaging incision 68 to provide a clear view of the surgical site. A surgeon may then separately rotate secondary actuator knob 20 to widen the incision of improve the angle of view. Surgical tissue retractor 10 can be mounted on a larger retractor such as a sternum or rib spreader retractor arm (not shown) by hanger 22.

FIG. 7 also includes an optional but preferred embodiment that allows surgical tissue retractor 10 to be easily manipulated and adjusted for placement in incision 68. In this embodiment hanger 22 is replaced by a socket 70 having a slot 71 (FIG. 8) for receiving a post 72 with base plate 78 attached by hinge 75 to a retractor rod 76.

The alternative embodiment is shown in greater detail in FIGS. 8 through 10. Socket 70 having slot 71 is formed on the rear of housing 11 of surgical tissue retractor 10. Socket 70 is constructed to receive base plate 78 on post 72 and is held in place by the frictional retention of ball 80 and spring 82 in bore 81. Post 72 engages slot 71 and is connected to retractor rod 76 by hinge 75 formed by tongue 84 engaging slot 86 on retractor rod 76 and held in place by pin 88.

Figure 11:
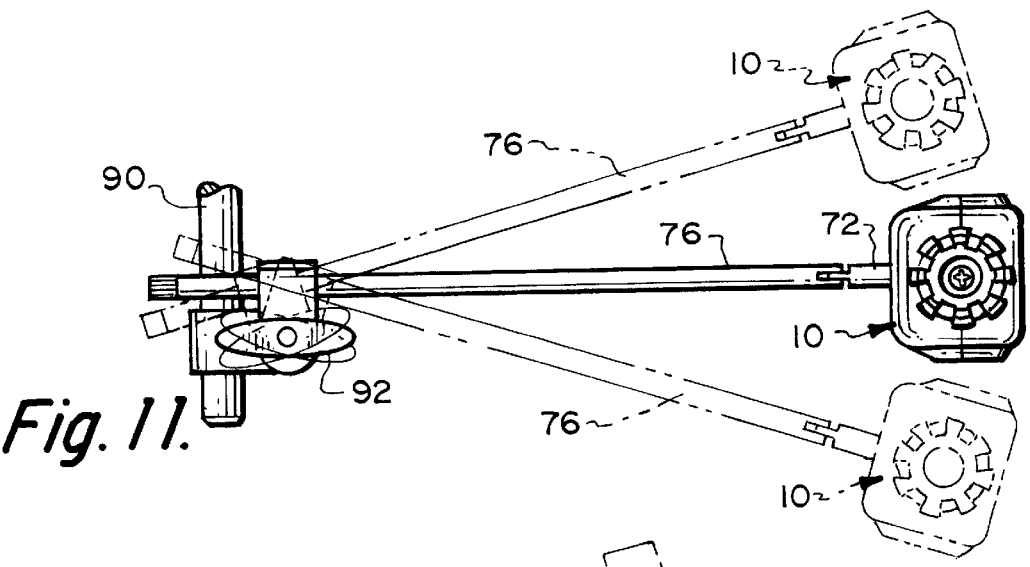
FIG. 11 is a top view of the surgical tissue retractor clamped on the arm of a larger retractor illustrating side-to-side adjustment.
Figure 12:
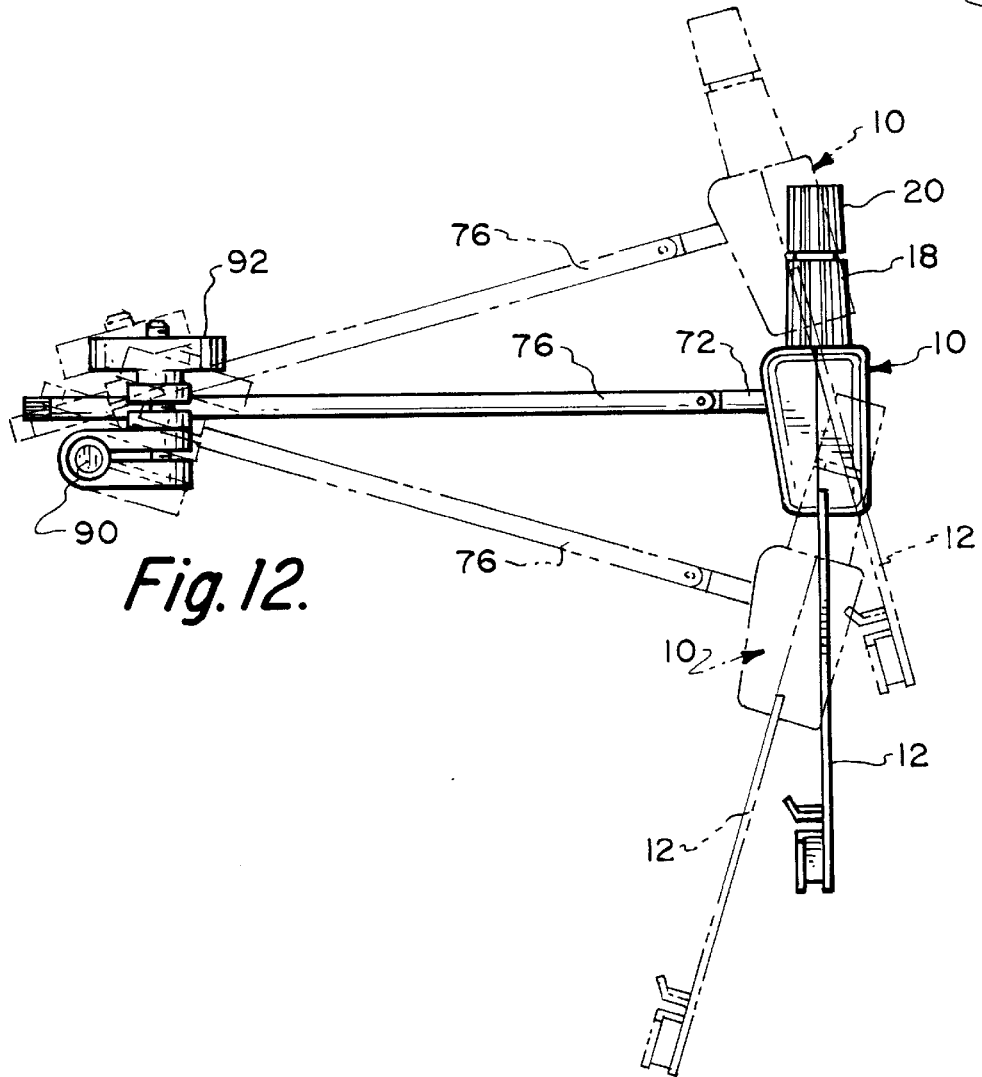
FIG. 12 is a side elevational view of the surgical tissue retractor clamped on the arm of a larger retractor illustrating vertical adjustment.

Surgical tissue retractor 10 functions as described previously but has the added versatility and movement illustrated in FIGS. 9, 11, and 12. Post 72 has a length that allows movement of surgical tissue retractor 10 to nearly parallel with retractor rod 76 in a vertical and side-to-side movement from nearly parallel to perpendicular to the retractor rod 76 as shown in FIG. 9.

The flexibility and wide range of movement for placement of surgical tissue retractor 10 is illustrated in FIGS. 11 and 12. Retractor rod 76 is clamped on a larger retractor arm 90 by conventional dual friction clamp 92 that allows adjustable side-to-side motion as illustrated in FIG. 11 or adjustable vertical motion as illustrated in FIG. 12. Surgical tissue retractor 10 can be rotated on base plate 78 as illustrated in FIG. 7, pivoted vertically on hinge 75 as illustrated in FIG. 9 or adjusted sideways and vertically as illustrated in FIGS. 11 and 12. This provides a wide range of adjustments and positioning of surgical tissue retractor 10 in an incision 68 before or after manipulation of primary retractor knob 18 and secondary retractor knob 20.

With the arrangement illustrated in the optional embodiment of FIGS. 7 through 12, surgical tissue retractor 10 may be placed in an incision 68 (FIG. 7) by manipulating and adjusting the retractor as shown in FIGS. 9, 11, and 12 with either side-to-side pivoting or swiveling motion. Primary retractor knob 18 and secondary retractor knob 20 may then be operated to expand or open retractor blades 12, 14, and 16 to provide a clear view through incision 68.

Surgical tissue retractor is mounted on retractor rod 76 by inserting base plate 78 in socket 70 as illustrated in FIG. 8 after retractor rod 76 clamped on retractor arm 90 as illustrated in FIG. 11. Base plate 78 seats in socket 70 with rod 72 engaging slot 71. Base plate 70 is securely retained in socket 70 by frictionally engaging ball 80 biased by spring 82 seated in bore 81 in post 72. Thus, surgical tissue retractor 10 is securely mounted on post 72 and retractor rod 76 but may be easily mounted or de-mounted.

Thus there has been described a unique and novel surgical tissue retractor having multiple blades that can be operated simultaneously or at least one blade can be operated independently. The blades are mounted in a housing for retraction by rotation of an actuator knob which withdraws an actuator tube to spread right and left retractor arms through actuator links. A center retractor blade is mounted on a threaded shaft in a secondary actuator knob attached to the actuator tube. This allows the center actuator blade to be operated simultaneously with the right and left side actuator blades or independently by rotation of the secondary actuator knob.

This invention is not to be limited by the embodiment shown in the drawings and described in the description which is given by way of example and not of limitation, but only in accordance with the scope of the appended claims.

What is claimed is:

1. A surgical tissue retractor comprising;
   a plurality of retractor blades;
   primary actuating means for simultaneously actuating said plurality of retractor blades to retract an incision;
   secondary actuating means for independently actuating at least one of said plurality of blades.

2. The surgical tissue retractor according to claim 1 in which said plurality of blades include a right side blade and left side blade connected to said primary actuating means.

3. The surgical tissue retractor according to claim 2 in which said primary actuating means comprises; a threaded actuating tube; link means linking said right and left side retractor blades to said threaded actuating tube; and a primary actuating knob threadably mounted on said threaded actuating tube; whereby rotation of said primary actuating knob opens or closes said plurality of retractor blades.

4. The surgical tissue retractor according to claim 3 in which said plurality of blades comprises three blades.

5. The surgical tissue retractor according to claim 4 in which said three blades include a center retractor blade; and connecting means connecting said center retractor blade to said threaded actuator tube for simultaneous operation of all three blades.

6. The surgical tissue retractor according to claim 5 in which said center blade may be extended or retracted independent of said right and left side retractor blades.

7. The surgical tissue retractor according to claim 5 in which said connecting means connecting said center blade to said primary threaded actuator tube comprises; a threaded shaft mounted on the end of said center retractor blade; said threaded shaft passing through said primary threaded actuator tube; and a secondary rotatable actuator knob attached to an end of said primary threaded knob; said threaded shaft on said end of said center retractor blade engaging threads in said secondary rotatable actuator knob; whereby said center retractor blade may be extended or retracted by rotation of said secondary actuator knob independent of said right and left side actuator blades.

8. The surgical tissue retractor according to claim 3 including mounting means for mounting said surgical tissue retractor on another retractor arm.

9. The surgical tissue retractor according to claim 8 in which said mounting means includes a housing for enclosing said threaded actuating tube and said link means; and a hanger on said housing for mounting said surgical tissue retractor on said another retractor arm.

10. The surgical tissue retractor according to claim 8 in which said mounting means comprises;
    a housing for enclosing said threaded actuating tube and said link means; and pivotal mounting means for pivotally mounting said surgical tissue retractor on said another retractor arm.

11. The surgical tissue retractor according to claim 10 in which said pivotal mounting means comprises; a socket on a surface of said housing; a retractor rod assembly engaging said socket; whereby said surgical tissue retractor may be mounted by clamping said retractor rod assembly to said another retractor arm.

12. The surgical tissue retractor according to claim 11 in which said retractor rod assembly comprises, a post having a base plate; said base plate engaging said socket on said housing; hinge means on said post; and a retractor rod connected to said post by said hinge means.

13. The surgical tissue retractor according to claim 12 in which said base plate is a circular base plate whereby said surgical tissue retractor may rotatably swivel on said post.

14. The surgical tissue retractor according to claim 13 including frictional retaining means for frictionally retaining said base plate in said socket on said housing.

15. The surgical tissue retractor according to claim 14 in which said frictional retaining means comprises a centrally located bore in said base plate; a ball in said bore; and biasing means biasing said ball into engagement with a surface in said socket.

* * * * *